(12) United States Patent
Yamasaki et al.

(10) Patent No.: US 7,182,744 B2
(45) Date of Patent: Feb. 27, 2007

(54) METHOD AND APPARATUS FOR ANEURISMAL TREATMENT

(75) Inventors: Sonny Yamasaki, Rohnert Park, CA (US); William F. Kaemmerer, Edina, MN (US)

(73) Assignee: Medtronic Vascular, Santa Rosa, CA (US)

( * ) Notice: Subject to any disclaimer, the term of this patent is extended or adjusted under 35 U.S.C. 154(b) by 264 days.

(21) Appl. No.: 10/423,302

(22) Filed: Apr. 25, 2003

(65) Prior Publication Data

US 2004/0215124 A1    Oct. 28, 2004

(51) Int. Cl.
| | |
|---|---|
| A61M 37/00 | (2006.01) |
| C02F 1/38 | (2006.01) |
| A61K 35/16 | (2006.01) |
| A61B 19/00 | (2006.01) |
| A61M 1/00 | (2006.01) |
| A31B 17/08 | (2006.01) |

(52) U.S. Cl. ............... 604/4.01; 604/28; 210/782; 424/529; 424/530; 128/898; 606/214

(58) Field of Classification Search ............... 604/4.01, 604/5.01, 6.04, 6.09, 6.16, 7–10, 19, 21, 604/27, 48, 500, 28, 96.01, 97.01, 264; 210/600, 210/634, 645, 781–2, 348, 359, 360.2; 424/429–532, 424/423, 425–6; 623/1.1, 1.42; 128/898; 606/213, 214; 514/1, 2
See application file for complete search history.

(56) References Cited

U.S. PATENT DOCUMENTS

| | | | | |
|---|---|---|---|---|
| 5,480,378 | A | * | 1/1996 | Weis-Fogh et al. ........ 604/6.04 |
| 5,785,679 | A | * | 7/1998 | Abolfathi et al. ........... 604/509 |
| 6,375,668 | B1 | * | 4/2002 | Gifford et al. ............... 606/200 |
| 6,726,674 | B2 | * | 4/2004 | Leu ....................... 604/101.01 |
| 6,942,692 | B2 | * | 9/2005 | Landau et al. ............. 623/1.35 |
| 6,960,352 | B2 | * | 11/2005 | Noujaim et al. ............ 424/423 |

OTHER PUBLICATIONS

Desmouliere et al., "*Transforming Growth Factor-β1 Induces α-Smooth Muscle Actin Expression In Granulation Tissue Myofibroblasts And In Quiescent And Growing Cultured Fibroblasts*" The Journal of Cell Biology, vol. 122, No. 1, 103-111, Jul. 1993.

Han et al., "*Recombinant Human Platelet-Derived Growth Factor And Transforming Growth Factor-β Mediated Contraction Of Human Dermal Fibroblast Populated Lattices Is Inhibited By Rho/GTPase Inhibitor But Does Not Require Phosphatldylinositol-3' Kinase*", Wound Repair and Regeneration, 10:169-176, 2002.

Liu et al., "*Persistence Of TGF-β1 Induction Of Increased Fibroblast Contractility*", In Vitro Cell Dev Biol. 37:193-201, Mar. 2001.

Vaughan et al., "*Transforming Growth Factor-β1 Promotes The Morphological And Functional Differentiation Of The Myofibroblast*", Experimental Cell Research, 257, 180-189, 2000.

Pandit et al., "*The Effect Of TGF-β Delivered Through A Collagen Scaffold On Wound Healing*", Journal of Investigative Surgery, 12:89-100, 1999.

Brown et al., "*Enhanced Fibroblast Contraction Of 3D Collagen Lattices And Integrin Expression By TGB-β1 And -β3: Mechanoregulatory Growth Factors?*", Experimental Cell Research, 274, 310-322, 2002.

de Gast et al., "*Transforming Growth Factor β-Coated Platinum Coils For Endovascular Treatment Of Aneurysms: An Animal Study*", Neurosurgery, 49:690-696, 2001.

Desfaits et al., "*Growth Factors Stimulate Neointimal Cells In Vitro And Increase The Thickness Of The Neointima Formed At The Neck Of Porcine Aneurysms Treated By Embolization*", Stroke, 31:498-507, 2000.

* cited by examiner

*Primary Examiner*—Tatyana Zalukaeva
*Assistant Examiner*—Leslie R. Deak

(57) ABSTRACT

An irritant or polymer is dispensed to the inner surface area of an aneurysm to exert a contractile force on the inner surface area of the aneurysm, thereby shrinking the aneurysm. As a result, the artery wall at the aneurysm site is strengthened, the risk of rupture is decreased, and at least a partial cure for the expansion of the arterial wall at the aneurysm site is provided.

12 Claims, 10 Drawing Sheets

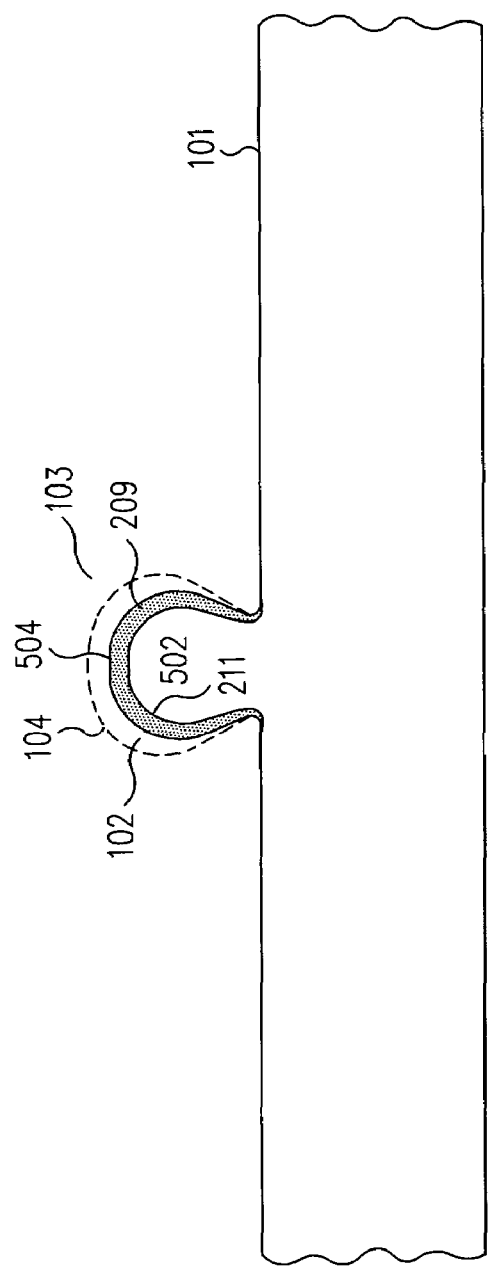
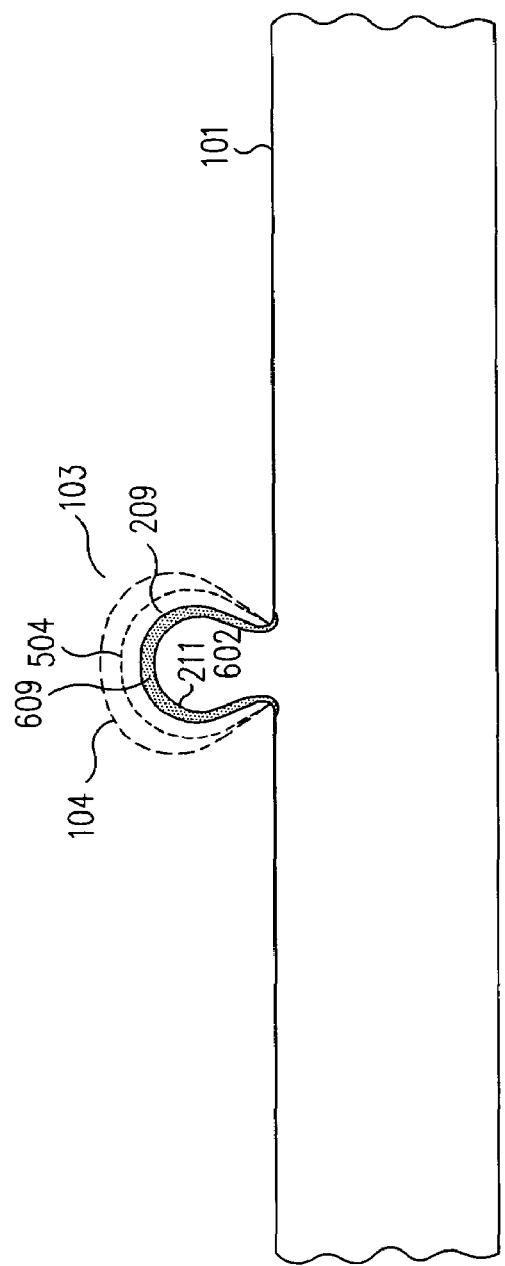

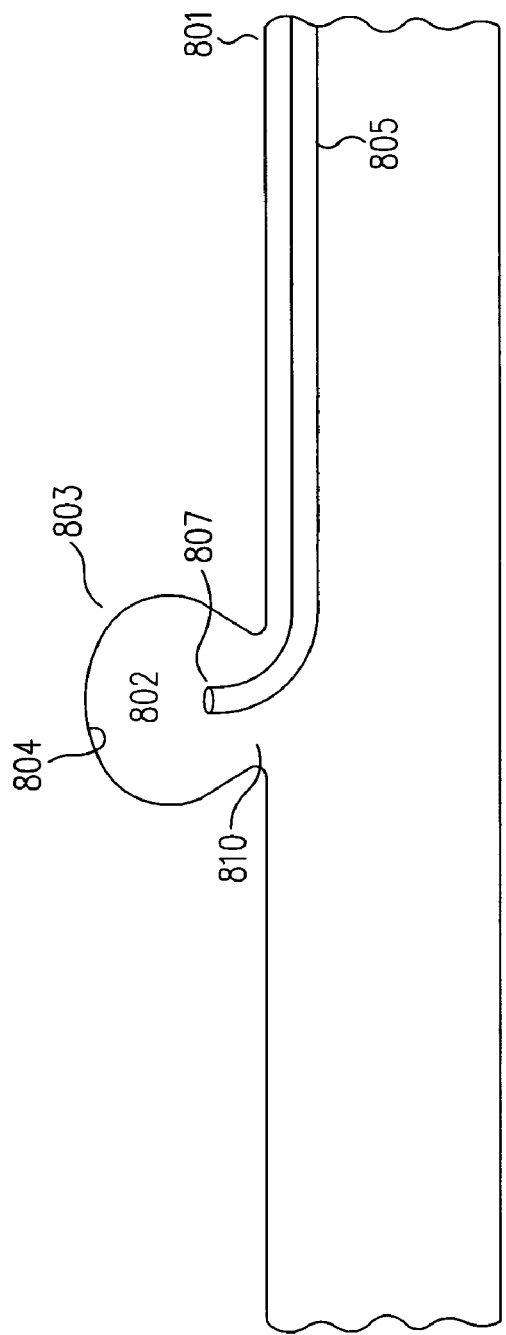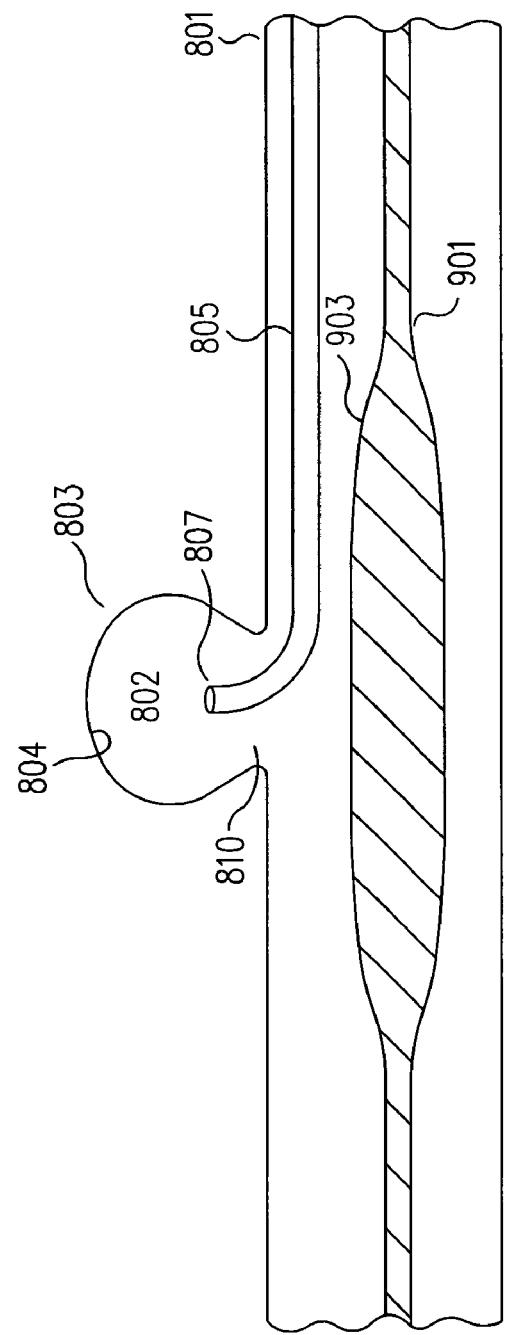

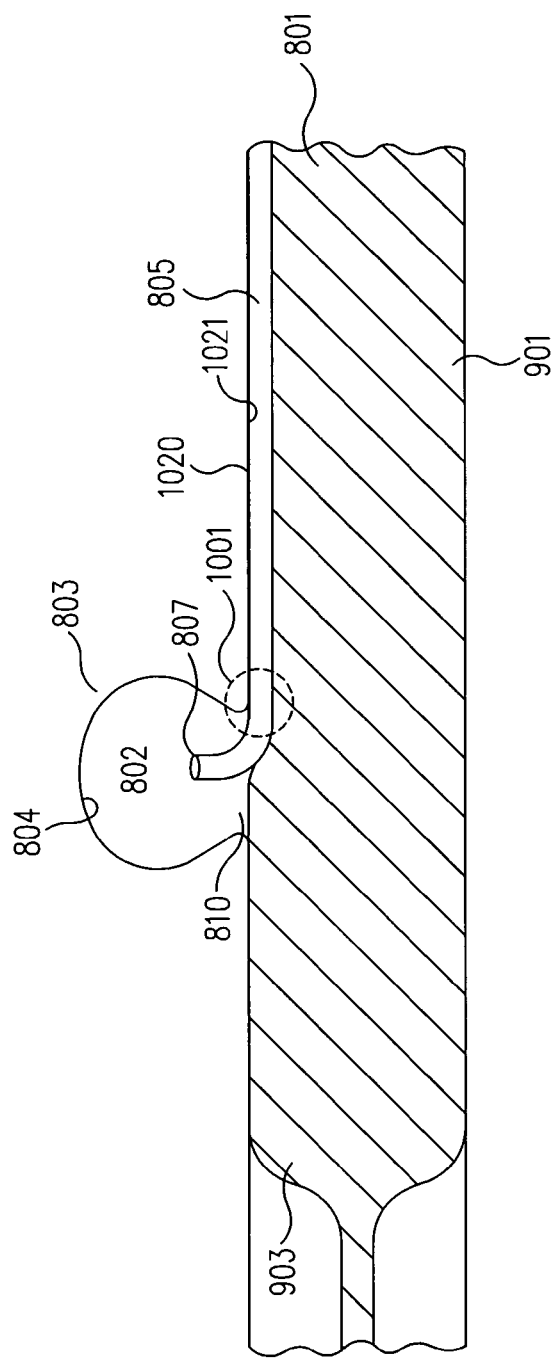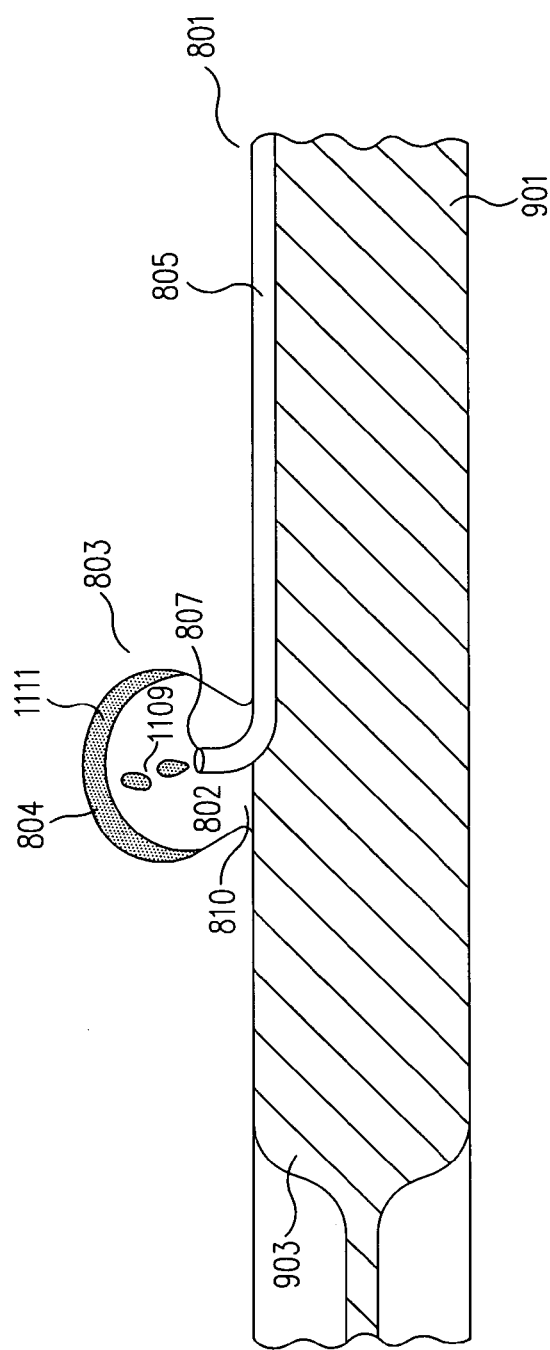

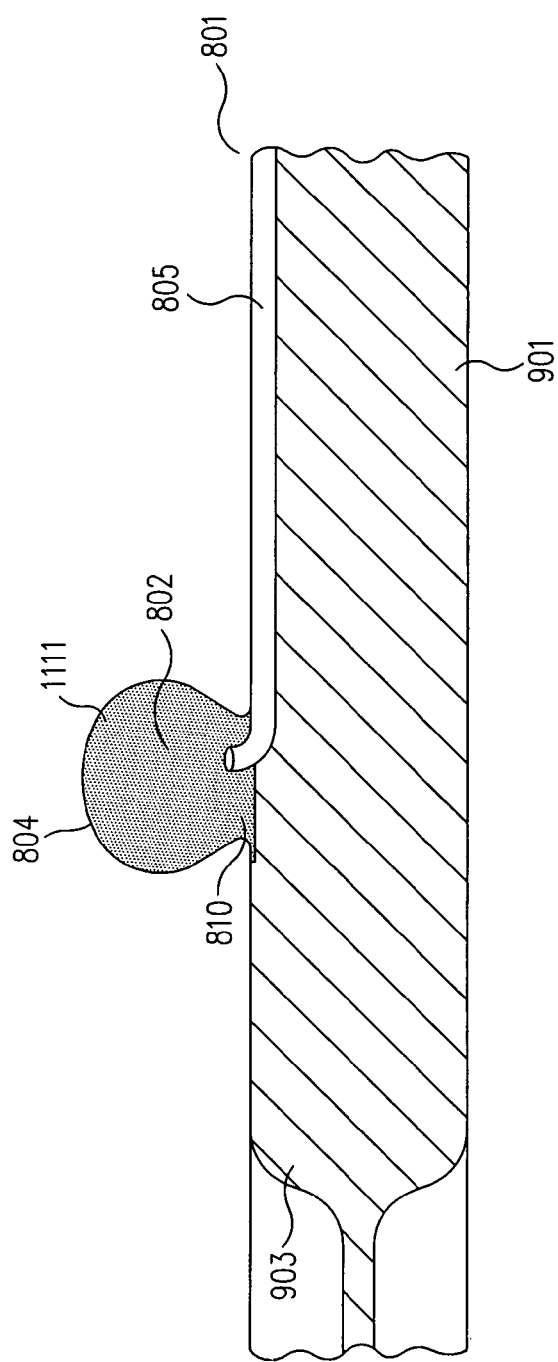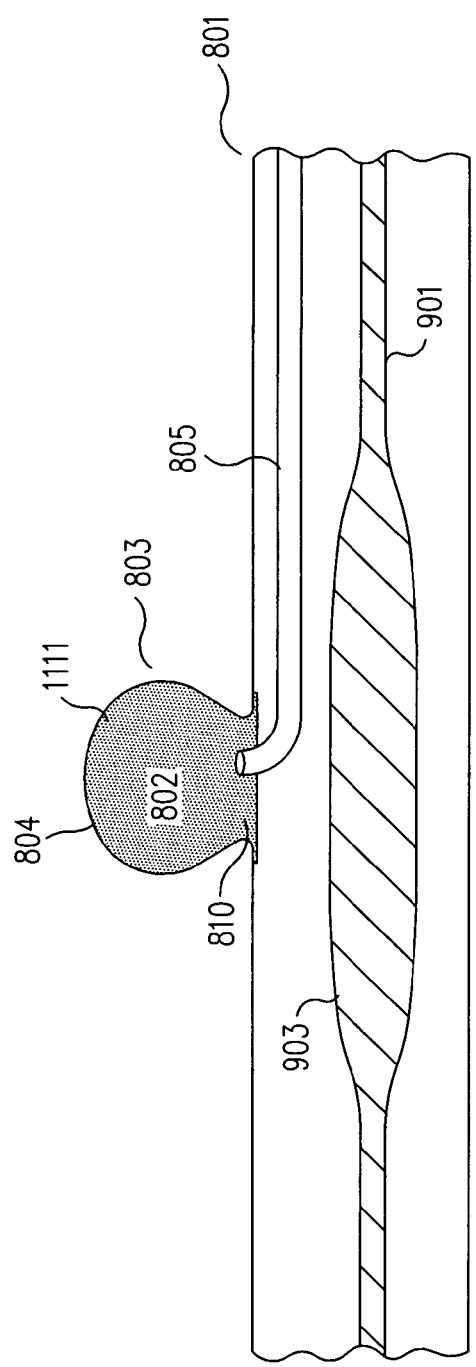

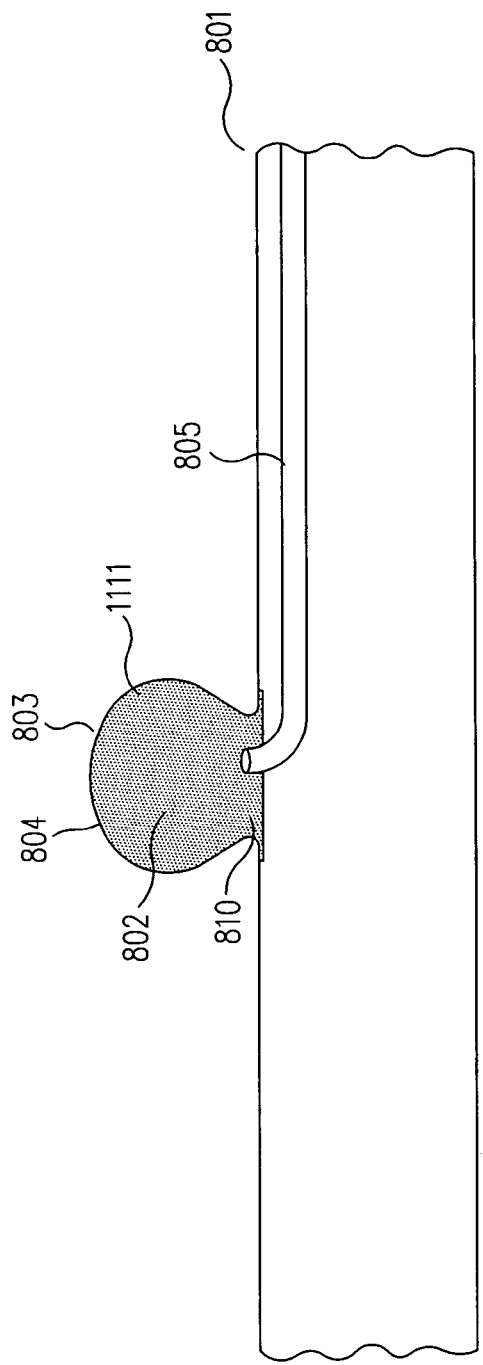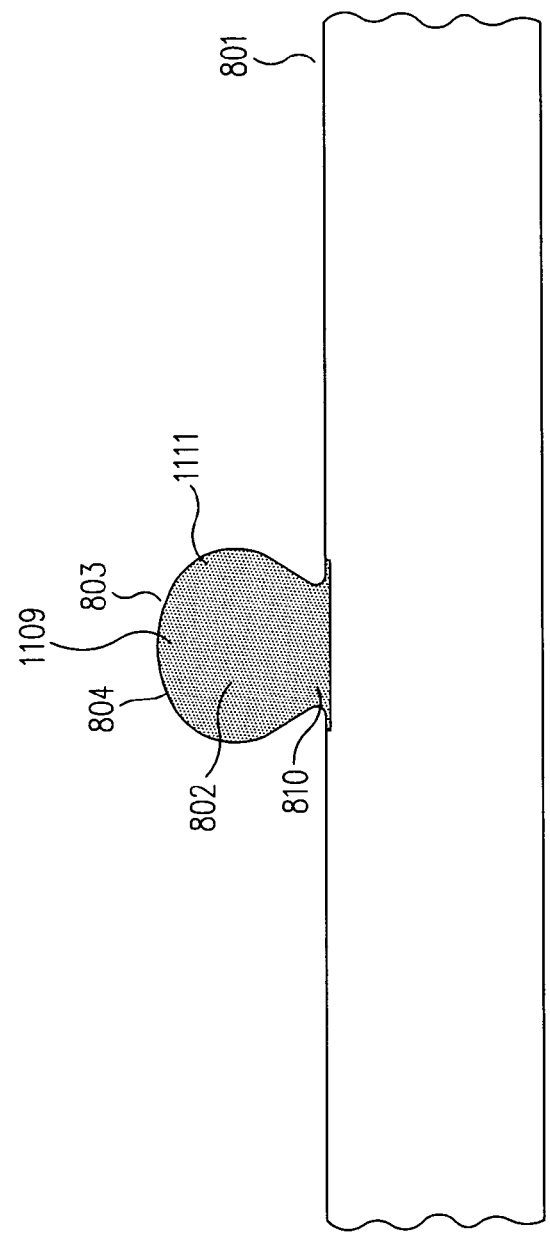

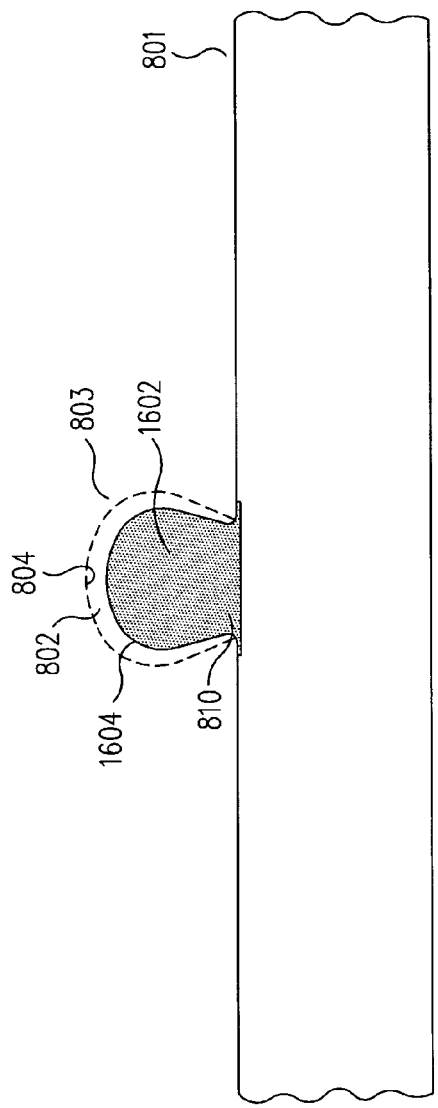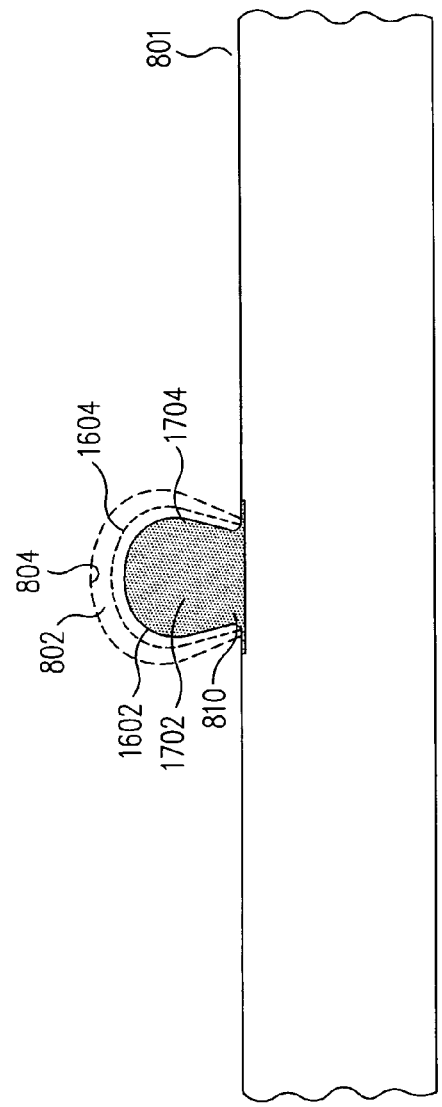
FIG. 16
FIG. 17

METHOD AND APPARATUS FOR ANEURISMAL TREATMENT

BACKGROUND OF THE INVENTION

1. Field of the Invention

The present invention relates to aneurismal treatments. More particularly, the present invention relates to methods for contracting and shrinking aneurysms.

2. Description of the Related Art

Vascular aneurysms are the result of abnormal dilation of a blood vessel, usually resulting from disease and/or genetic predisposition, which weakens the arterial wall and allows it to expand. The weakened areas of the arterial wall caused by an aneurysm are problematic because they are subject to rupture and if a rupture occurs, the aneurysm can prove fatal.

In the prior art, several procedures and methods have been established for the exclusion of aneurysms. One such method involved the insertion of a coil within the aneurysm itself. Using prior art coil insertion methods, the coil precipitated the formation of a thrombus, or clot, within the aneurysm. The thrombus then partially, or completely, occluded the aneurysm. In this manner, blood from the parent artery (or vessel) was prevented from flowing into, and circulating within, the aneurysm. Consequently, pressure on the weakened arterial wall at the aneurysm site was reduced, as was the risk of rupture.

While at times an effective treatment, the prior art coil insertion method suffered from several drawbacks. First, there was a risk of the coil, or ensuing thrombus, migrating from the aneurysm to the parent artery or vessel and causing a thrombo-embolic stroke. To minimize this risk, the prior art coil insertion method was typically limited to the treatment of saccular aneurysms having small necks to ensure that, once inserted, the coil remained within the aneurysm. In addition, wide-necked and fusiform aneurysms were also difficult to treat effectively with prior art coil insertion methods. Another disadvantage of prior art coil insertion methods was that the coils could rupture the aneurysm by poking through the aneurysm wall, resulting in life-threatening subarachnoid hemorrhage.

In addition, the effectiveness of the prior art coil insertion method discussed above was limited by the fact that while the insertion of the coil, and the resulting thrombus, could result in protecting the arterial wall at the aneurysm site, the method did not promote shrinkage of the aneurysm, or in any way address the expansion of the arterial wall at the aneurysm site.

One common result using prior art methods was compaction of the coils within the aneurysm within the 3-month follow-up period. If left untreated, the aneurysm could then continue to enlarge, and the risk of rupture remained. By not shrinking the aneurysm, prior art coil insertion methods often resulted in the coils ending up contributing to the "mass effect", in which the aneurysm pressed against adjacent structures such as cranial nerves, other vessels, and the brain parenchyma.

In short, the prior art coil insertion method treated the symptom but did nothing to provide a cure, or partial cure, for the expansion of the arterial wall at the aneurysm site.

In addition, since the coils used with the prior art coil insertion method had to be of a minimum size, typically three millimeters or more, to perform their function and, since the coils had to be inserted into the aneurysm site, the prior art method could only be used on relatively large aneurysms, i.e., aneurysms having diameters of three millimeters or more. Therefore, the prior art coil insertion method typically could not be used on smaller aneurysms, such as those that might be advantageously found by early detection. Consequently, in the prior art, many aneurysms had to be either treated by more intrusive, and potentially dangerous, methods or, in some cases, the patient would simply have to wait until the aneurysm was large enough to allow treatment using the prior art coil insertion method. Since, as discussed above, aneurysms can result in a rupture of the arterial wall, and possibly death, waiting for the aneurysm to expand before treating it was not a desirable situation.

In addition to prior art coil insertion methods for excluding aneurysms, other prior art methods have been established for the exclusion of aneurysms including the use of liquid embolics such as MTI's Onyx and the various methacrylates. However, like the prior art coil insertion methods, these other prior art methods treated the symptom but did nothing to shrink the aneurysm or provide a cure, or partial cure, for the expansion of the arterial wall at the aneurysm site.

What is needed is a method for treating aneurysms of all sizes that promotes shrinkage of the aneurysm in addition to strengthening of the arterial wall at the aneurysm site.

SUMMARY OF THE INVENTION

Using the methods of embodiments in accordance with the present invention, the inner surface area of an aneurysm is forced to contract, thereby shrinking the aneurysm. Consequently, using the method according to embodiments of the present invention, the artery wall is strengthened, the risk of rupture is decreased, and at least a partial cure for the expansion of the arterial wall at the aneurysm site is provided.

In one example, an irritant is provided to force the contraction of the aneurysm. In one example, a micro-catheter is inserted into a patient's parent artery or vessel and positioned at the aneurysm site with the micro-catheter tip and micro-catheter lumen in the aneurysm. Once the micro-catheter and micro-catheter tip and lumen are properly positioned, an irritant, typically in serum form, is dispensed into aneurysm through the micro-catheter. Once the irritant is dispensed, the micro-catheter is removed.

In one example, the irritant is chosen such that the irritant promotes a contraction or shrinkage of the aneurysm by causing a contractile force to be exerted on the aneurysm inner surface area. In one example, the irritant is a serum containing the inflammatory cytokine "Transforming Growth Factor-Beta" (TGF-beta) and collagen. As discussed in more detail below, TGF-beta promotes the expression of smooth muscle actin fibrils in fibroblasts, and the subsequent contractile force exerted by those fibroblasts against a collagen matrix. Consequently, in one example, TGF-beta and collagen are introduced in the aneurysm to shrink the aneurysm.

In addition, in one example, a radiopaque marker is added to the solution at 10% to 50% of the usual concentration (i.e., 5% to 25%) to facilitate visualization of the irritant solution, and still differentiate it from the contrast injected into the parent artery during the procedure.

In one example, a remodeling balloon is used to isolate or "occlude" the aneurysm while the irritant is applied in order to coat the neck of the aneurysm as well. In this example, depending on the viscosity and adherence properties of the irritant, the remodeling balloon is inflated to occlude the aneurysm and then the aneurysm is completely filled with irritant. The irritant is ten left in place in the occluded aneurysm for a predetermined time after which the excess irritant is aspirated and the remodeling balloon is deflated and removed.

In another example, a polymer material is used to contract or "shrink" the aneurysm instead of an irritant. In this example, the polymer is dispensed into an aneurysm, typically in a liquid or gel form, where it adheres to the inner surface of the aneurysm. In one example, the polymer is chosen so that the polymer contracts or "shrinks" as it cures and hardens into its solid or semi-solid form. Since, in one example, the polymer adheres to the inner surface of the aneurysm, the aneurysm also contracts or "shrinks" with the polymer as the polymer cures and hardens.

In addition, in one example, a radiopaque marker is added to the polymer, while the polymer is in liquid or gel form, and prior to the polymer being dispensed, at 10% to 50% of the usual concentration to facilitate visualization of the polymer, and still differentiate it from the contrast injected into the parent artery during the procedure.

As discussed in more detail below, in one example, a remodeling balloon is used to isolate or "occlude" the aneurysm while the polymer is being dispensed and cured.

In contrast to the prior art methods, the present invention is specifically directed to shrinking the aneurysm thereby providing at least a partial cure for the expansion of the arterial wall at the aneurysm site and potentially reducing neurological effects due to a brain aneurysm. This is significant since, shrinking the aneurysm wall strengthens the aneurysm wall and reduces the risk of rupture. Specifically, $P=T(1/R1+1/R2)$, where P=transmural pressure across the aneurysm wall, T is the tension in the wall, R1 & R2 are the principal radii of curvature. If we assume a spherical aneurysm (R1=R2), then the equation becomes $P=2T/R$, or put another way, $T=PR/2$. This means that as the aneurysm shrinks, the radius decreases and the tension in the wall decreases (the transmural pressure remains essentially the same before and after treatment). This effect is even greater for a cylindrical tube (like an artery) where R2 is infinite. Then 1/R2 approaches 0, and the equation becomes $P=T(1/R)$, or $T=PR$. Now the tension in the wall decreases twice as much for a given decrease in radius (compared to the sphere). Consequently, in contrast to the prior art, the method in accordance with the present invention addresses the underlying disease rather than simply treating the symptom.

In addition, in embodiments in accordance with the present invention, there are no coils used and therefore no risk of the coil, or ensuing thrombus, migrating from the aneurysm to the parent artery or vessel and causing a thrombo-embolic stroke or of the coil compacting and/or rupturing the aneurysm wall. Consequently, the method according to the invention is safer than prior art methods and can be applied to more types and shapes of aneurysms than prior art methods In addition, embodiments in accordance with the present invention can be used on aneurysms of all sizes and shapes and any aneurysm can be treated using the method according to the present invention as soon as it is detected. In addition, embodiments in accordance with the present invention can be used to treat any type of aneurysm including brain aneurysms, abdominal aneurysms and thoracic aortic aneurysms. The fact that the present invention allows for early and immediate treatment provides the method according to the present invention with a significant advantage over the prior art.

BRIEF DESCRIPTION OF THE DRAWINGS

FIG. 5 is a side view, in cross-section, of the parent artery or vessel at the aneurysm site with irritant at least partially coating the inner surface area of the aneurysm and the resulting partial shrinkage of the aneurysm;

FIG. 6 is a side view, in cross-section, of the parent artery or vessel at the aneurysm site with irritant at least partially coating the inner surface area of the aneurysm and the resulting shrinkage of the aneurysm;

FIG. 8 is a side view, in cross-section, of a parent artery or vessel at an aneurysm site including a micro-catheter inserted into the aneurysm for dispensing a polymer into the aneurysm;

FIG. 9 is a side view, in cross-section, of the parent artery or vessel at the aneurysm site including a micro-catheter inserted into the aneurysm for dispensing a polymer into the aneurysm and an un-inflated remodeling balloon inserted into the artery or vessel for isolating the aneurysm site;

FIG. 10 is a side view, in cross-section, of the parent artery or vessel at the aneurysm site including a micro-catheter inserted into the aneurysm for dispensing a polymer into the aneurysm and an inflated remodeling balloon inserted into the artery or vessel for isolating the aneurysm site;

FIG. 11 is a side view, in cross-section, of the parent artery or vessel at the aneurysm site including a micro-catheter inserted into the aneurysm dispensing a polymer into the aneurysm and an inflated remodeling balloon inserted into the artery for isolating the aneurysm site;

FIG. 12 is a side view, in cross-section, of the parent artery or vessel at the aneurysm site including a micro-catheter inserted into the aneurysm after the micro-catheter has dispensed a polymer into the aneurysm and an inflated remodeling balloon inserted into the artery for isolating the aneurysm site;

FIG. 13 is a side view, in cross-section, of the parent artery or vessel at the aneurysm site including a micro-catheter inserted into the aneurysm after having dispensed a polymer into the aneurysm and a deflated remodeling balloon inserted into the a parent artery or vessel;

FIG. 14 is a side view, in cross-section, of the parent artery or vessel at the aneurysm site including a micro-catheter inserted into the aneurysm after having dispensed a polymer into the aneurysm and after removing the deflated remodeling balloon from the parent artery or vessel;

FIG. 15 is a side view, in cross-section, of the parent artery or vessel at the aneurysm site after the micro-catheter has been removed;

FIG. 16 is a side view, in cross-section, of the parent artery or vessel at the aneurysm site with a polymer that has been dispensed into the aneurysm and the resulting partial shrinkage of the aneurysm; and FIG. 17 is a side view, in cross-section, of the parent artery or vessel at the aneurysm site with a polymer that has been dispensed into the aneurysm and the resulting shrinkage of the aneurysm.

Common reference numerals are used throughout the drawings and detailed description to indicate like elements.

DETAILED DESCRIPTION

In embodiments in accordance with the present invention, the inner surface area of an aneurysm (103 in FIGS. 1 to 6 and 803 in FIGS. 8 to 14) is forced to contract thereby shrinking the aneurysm (FIGS. 5, 6, 16 and 17). Consequently, using the method according to the invention, the artery wall is strengthened, the risk of rupture is decreased, and at least a partial cure for the expansion of the arterial wall at the aneurysm site is provided.

Figure 2:
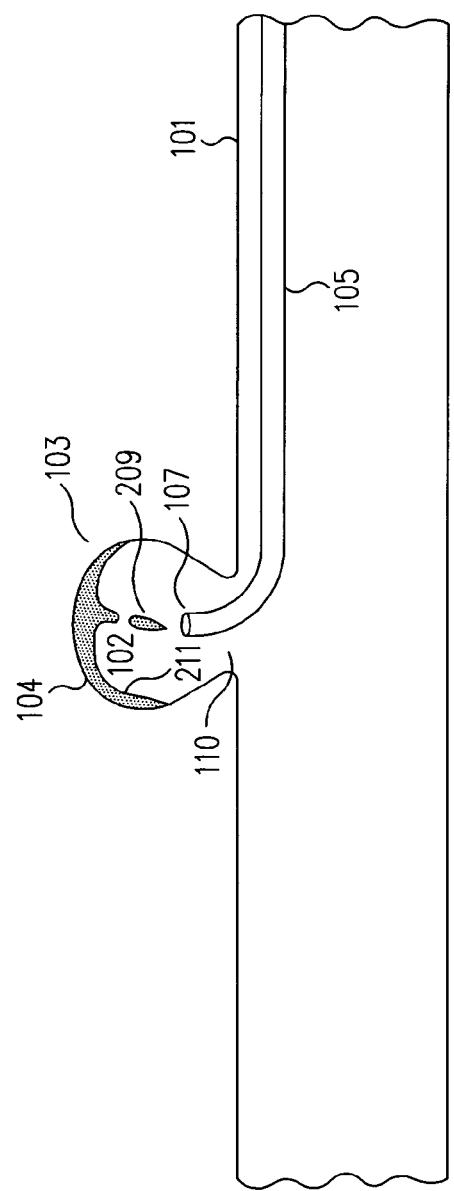
FIG. 2 is a side view, in cross-section, of the parent artery or vessel at the aneurysm site including a micro-catheter inserted into the aneurysm dispensing an irritant into the aneurysm.
Figure 3:
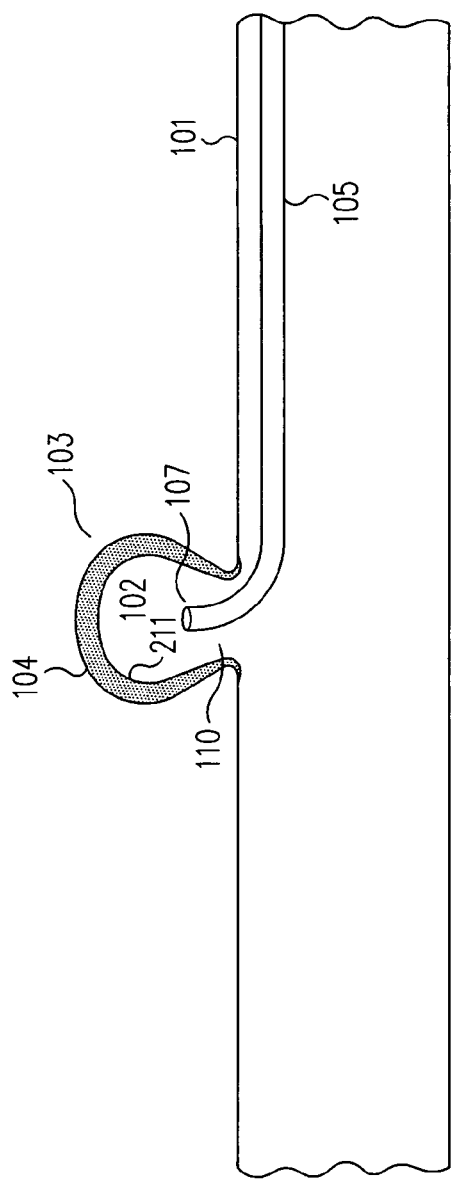
FIG. 3 is a side view, in cross-section, of the parent artery or vessel at the aneurysm site including a micro-catheter inserted into the aneurysm after the micro-catheter has dispensed an irritant into the aneurysm.
Figure 4:
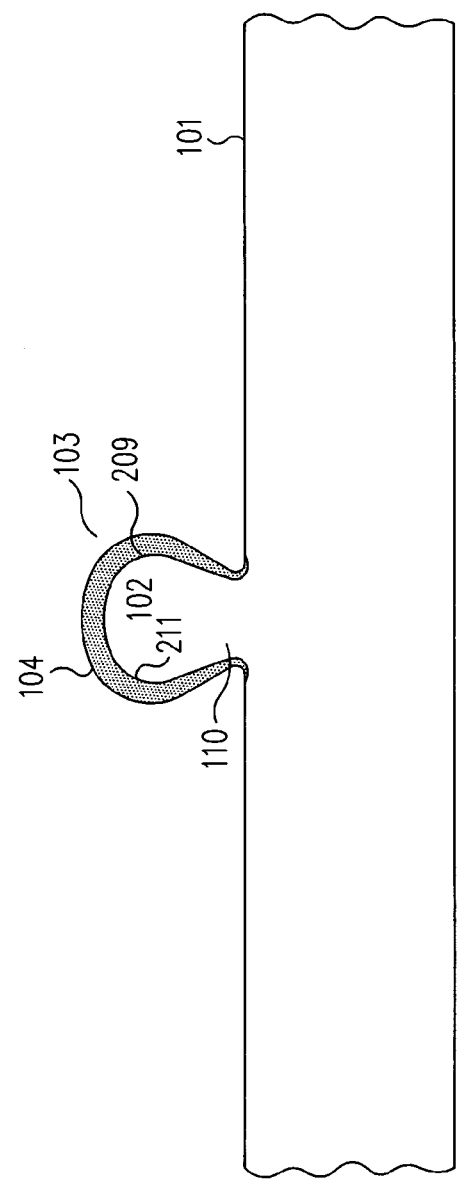
FIG. 4 is a side view, in cross-section, of the parent artery or vessel at the aneurysm site with irritant at least partially coating the inner surface area of the aneurysm.

In one example, an irritant (209 in FIGS. 2, 3, 4, 5, and 6) is provided to force the contraction of the aneurysm (103 in FIGS. 1 to 6). A micro-catheter (105 in FIGS. 1, 2 and 3) is inserted into a patient's parent artery or vessel (101 in FIGS. 1 to 6) and positioned at the aneurysm site with the micro-catheter lumen (107 in FIGS. 1, 2 and 3) in the aneurysm. Once the micro-catheter and micro-catheter tip and lumen are properly positioned, an irritant (209 in FIGS. 2, 3, 4, 5, and 6), typically in serum form, is dispensed into the aneurysm through the micro-catheter. Once the irritant is dispensed, the micro-catheter is removed (FIGS. 4, 5 and 6).

The irritant is chosen such that the irritant promotes a contraction or shrinkage of the aneurysm by causing a contractile force to be exerted on the aneurysm inner surface area. In one example, the irritant is a serum containing the inflammatory cytokine "Transforming Growth Factor-Beta" (TGF-beta) and collagen (707 in FIG. 7A). As discussed in more detail below, TGF-beta promotes the expression of smooth muscle actin fibrils in fibroblasts, and the subsequent contractile force exerted by those fibroblasts against a collagen matrix. Consequently, when TGF-beta and collagen are dispensed onto aneurysm inner surface area as part of the irritant, a contractile force is exerted by fibroblasts against the collagen matrix and the original aneurysm inner surface area and volume contract or "shrink".

In addition, in one example, a radiopaque marker contrast is added to the irritant at 10% to 50% of the usual concentration to facilitate visualization of the irritant, and still differentiate it from the contrast injected into the parent vessel during the procedure.

In another example (FIGS. 8 to 17), a polymer (1109 in FIGS. 11 to 17) is used to contract or "shrink" the aneurysm (803 in FIGS. 8 to 17) instead of an irritant. According this embodiment, the polymer is dispensed into an aneurysm in liquid form where it adheres to the aneurysm inner surface area (804 in FIGS. 8 to 17). The polymer is chosen so that the polymer contracts or "shrinks" as it cures and hardens into its solid or semi-solid form. In one example, the polymer is a hydrophylic polymer gel with hydroxl or carboxl groups on the surface. One example of a hydrophylic polymer gel with hydroxl or carboxl groups on the surface is polyhydroxyethylmethacrylate. In other examples, the polymer can include an alginate gel or a hyaluronic acid. Other suitable polymers include silicone, urethane, epoxy, and polymethyl methacrylate(PMMA). In other examples, poly tetra flourethylene (PTFE, Teflon), polyethylene, polypropylene, polysulfone are the polymers used. In general, any of the polymers of the epoxy, urethane, and silicone type can potentially be used. In addition, a biodegradable polymer such as the polycarprolatone (PCL) polymers can be used.

Since, in one example, the polymer adheres to the aneurysm inner surface area, the aneurysm also contracts or "shrinks" with the polymer as the polymer cures and hardens.

In addition, in one example, a radiopaque marker (not shown) is added to the polymer, while the polymer is in liquid or gel form, and prior to the polymer being dispensed, at 10% to 50% of the usual concentration to facilitate visualization of the polymer, and still differentiate it from the contrast injected into the parent vessel during the procedure.

As discussed in more detail below, in one example, a remodeling balloon (901 in FIGS. 9, 10, 11 and 12) is used to isolate or "occlude" the aneurysm while the polymer is being dispensed and cured.

As discussed above, a micro-catheter is inserted into a patient's parent artery or vessel and positioned at the aneurysm site with the micro-catheter tip and lumen in the aneurysm. Micro-catheters, their use, and their operation are well known to those of skill in the art. Consequently, the structure, insertion, positioning and use of a micro-catheter are not described in detail herein to avoid detracting from the present invention.

In addition, as discussed in more detail below, in one example, the aneurysm is cleansed of any blood trapped in the aneurysm prior to, or during, the application of the irritant or polymer. In one example, the cleansing of the aneurysm is accomplished by employing a dual lumen micro-catheter with the invention such that recovery of any blood trapped in the aneurysm can occur via one lumen, while the irritant or polymer is delivered via the other. In another example, the cleansing of the aneurysm is accomplished before the delivery of the irritant or polymer by either a single or dual lumen micro-catheter. However, even in this example, a dual lumen micro-catheter may be desired, despite the sequential sequencing, to ensure the removed blood will "clear" the micro-catheter lumen and allow passage of the irritant or polymer. In yet other examples, the cleansing of the aneurysm is not performed at all. In these examples, the micro-catheter is positioned, and the irritant or polymer is dispensed at a pressure, such that the irritant or polymer displaces, and replaces, any trapped blood. This procedure is possible because most remodeling balloons are highly compliant balloons with nominal inflation pressures of 0.5 ATM. Dual lumen micro-catheters, their use, and their operation are well known to those of skill in the art and the particular processes for cleansing trapped blood from an aneurysm is not a significant element of the present invention. Consequently, the structure, insertion, positioning and use of a dual lumen micro-catheter and the cleansing process discussed above are not described in more detail herein to avoid detracting from the present invention.

Figure 1:
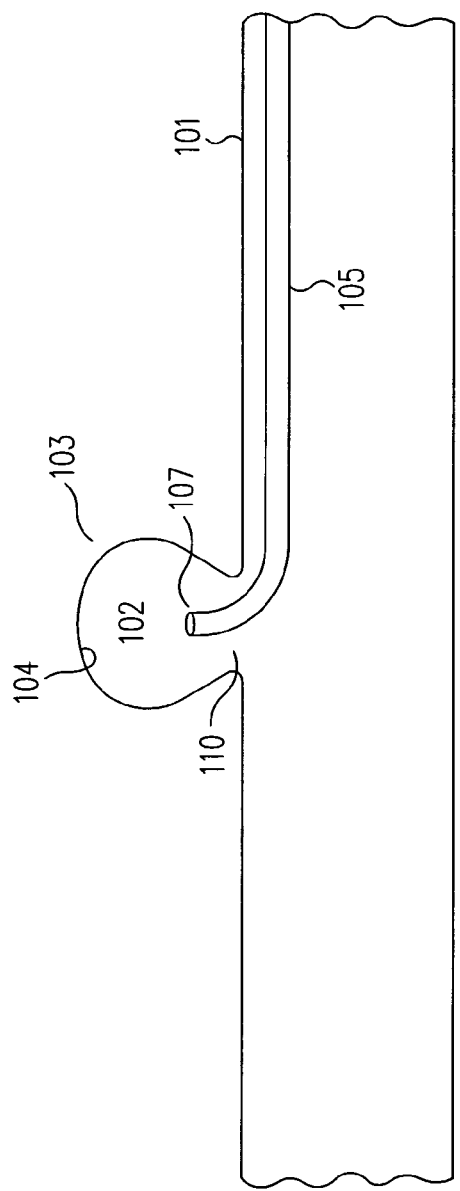
FIG. 1 is a side view, in cross-section, of a parent artery or vessel at an aneurysm site including a micro-catheter inserted into the aneurysm for dispensing an irritant into the aneurysm.

FIG. 1 is a side view, in cross-section, of a patient's parent artery or vessel 101 at an aneurysm 103 site including a micro-catheter 105 inserted into aneurysm 103 for dispensing an irritant. As discussed above, in one example, aneurysm 103 is cleansed of any blood (not shown) trapped in aneurysm 103 prior to, or during, the application of the irritant. In one example, the cleansing of aneurysm 103 is accomplished by employing a dual lumen micro-catheter (not shown) as micro-catheter 105 such that recovery of any blood (not shown) trapped in aneurysm 103 can occur via one lumen (not shown), while the irritant is delivered via the other. In another example, the cleansing of aneurysm 103 is accomplished by methods well known to those of skill in the art before the delivery of the irritant by either a single or dual lumen catheter.

As seen in FIG. 1, in one example, once aneurysm 103 is cleansed of any trapped blood, micro-catheter 105 is positioned to extend into neck 110 of aneurysm 103 such that micro-catheter tip 107 is positioned within aneurysm 103. As shown in FIG. 1, aneurysm 103 has an original, or first, aneurysm inner surface area 104 enclosing an original, or first, aneurysm volume 102. Once micro-catheter 105 and micro-catheter tip 107 are positioned as shown in FIG. 1, an irritant, typically in serum form, is dispensed into aneurysm 103 through micro-catheter 105 and micro-catheter tip 107.

FIG. 2 is a side view, in cross-section, of parent artery or vessel 101 at aneurysm 103 site including micro-catheter 105 inserted into aneurysm 103 and dispensing an irritant 209, typically in serum form, from micro-catheter tip 107 onto original aneurysm inner surface area 104 and onto neck 110 of aneurysm 103. In one example, irritant 209 is chosen such that irritant 209 promotes a contraction or "shrinkage" of aneurysm 103 by causing a contractile force to be exerted on original aneurysm inner surface area 104. One type of irritant 209 suitable for use with the present invention is discussed in more detail below with respect to FIGS. 7A and 7B.

FIG. 3 is a side view, in cross-section, of parent artery or vessel 101 at aneurysm 103 site including micro-catheter 105 inserted into aneurysm 103 after micro-catheter 105 has completed dispensing irritant 209 into aneurysm 103 in a thin layer 211 substantially covering original aneurysm inner surface area 104. As shown in FIGS. 1 to 6, irritant 209 is dispensed from micro-catheter tip 107 to original aneurysm inner surface area 104 and neck 110 of aneurysm 103 in a relatively thin layer 211. In another embodiment, irritant 209 is dispensed from micro-catheter tip 107 to partially, or substantially fill, original aneurysm volume 102. In yet another example (not shown), irritant 209 is put in contact with original aneurysm inner surface area 104 by coating elements (not shown), such as prior art coils or other media, with irritant 209 and inserting the coated elements into aneurysm 103.

In one example (not shown), a remodeling balloon (not shown), such as remodeling balloon 901 shown in FIGS. 9 to 13 and discussed below with respect to FIGS. 9 to 13, is used to temporarily isolate or "occlude" aneurysm 103 while aneurysm 103 is filled with irritant 209. In this example, the remodeling balloon (not shown) is inflated and irritant is dispensed into aneurysm 103, completely filling aneurysm 103. Irritant 209 and the remodeling balloon (not shown) are then left in place, isolating aneurysm 103 filled with irritant 209 for a predetermined time, typically a few minutes. Then the excess irritant 209 is aspirated.

Once irritant 209 has been dispensed from micro-catheter 105, micro-catheter 105 is removed from parent artery or vessel 101. FIG. 4 is a side view, in cross-section, of parent artery or vessel 101 at aneurysm 103 site with irritant 209 substantially coating original aneurysm inner surface area 104 of aneurysm 103 in a thin layer 211.

Once irritant 209 substantially coats original aneurysm inner surface area 104 and neck 110 of aneurysm 103 in a thin layer 211 as shown in FIG. 4, aneurysm 103 begins to contract. FIG. 5 is a side view, in cross-section, of parent artery or vessel 101 at aneurysm 103 site with irritant 209 substantially coating the partially contracted aneurysm inner surface area 504 of aneurysm 103. As discussed above, in one example, irritant 209 is chosen such that irritant 209 promotes a contraction or shrinkage of aneurysm 103 by causing a contractile force to be exerted on original aneurysm inner surface area 104 such that, over time, original aneurysm inner surface area 104, enclosing original aneurysm volume 102, contracts or "shrinks" down to partially contracted aneurysm inner surface area 504, enclosing partially reduced aneurysm volume 502. As also noted above, one type of irritant 209 suitable for use with the present invention is discussed in more detail below with respect to FIGS. 7A and 7B.

As time passes, in some instances as much as two or more weeks, irritant 209 causes further contraction or "shrinkage" of partially contracted aneurysm inner surface area 504. FIG. 6 is a side view, in cross-section, of parent artery or vessel 101 at aneurysm 103 site with irritant 209 substantially coating the contracted, or second, aneurysm inner surface area 604 of aneurysm 103. As shown in FIG. 6, over time, partially contracted aneurysm inner surface area 504, enclosing partially reduced aneurysm volume 502, further contracts or "shrinks" down to contracted aneurysm inner surface area 604 enclosing reduced, or second, aneurysm volume 602. According to one example, original, or first, aneurysm volume 102 is reduced four to fifty percent or more to contracted, or second, aneurysm volume 602.

As discussed above, irritant 209 is chosen such that irritant 209 promotes a contraction or shrinkage of aneurysm 103 by causing a contractile force to be exerted on aneurysm inner surface area 104. In one embodiment, the inflammatory cytokine "Transforming Growth Factor-Beta" (TGF-beta) and collagen are delivered in serum form to original aneurysm inner surface area 104 as part of irritant 209. TGF-beta promotes the expression of smooth muscle actin fibrils in fibroblasts, and the subsequent contractile force exerted by those fibroblasts against a collagen matrix. This process is part of the contraction element of normal wound healing. Consequently, when TGF-beta and collagen are dispensed onto original aneurysm inner surface area 104 as part of irritant 209, a contractile force is exerted by fibroblasts against the collagen matrix to "shrink" original aneurysm inner surface area 104 and original aneurysm volume 102.

Figure 7A:
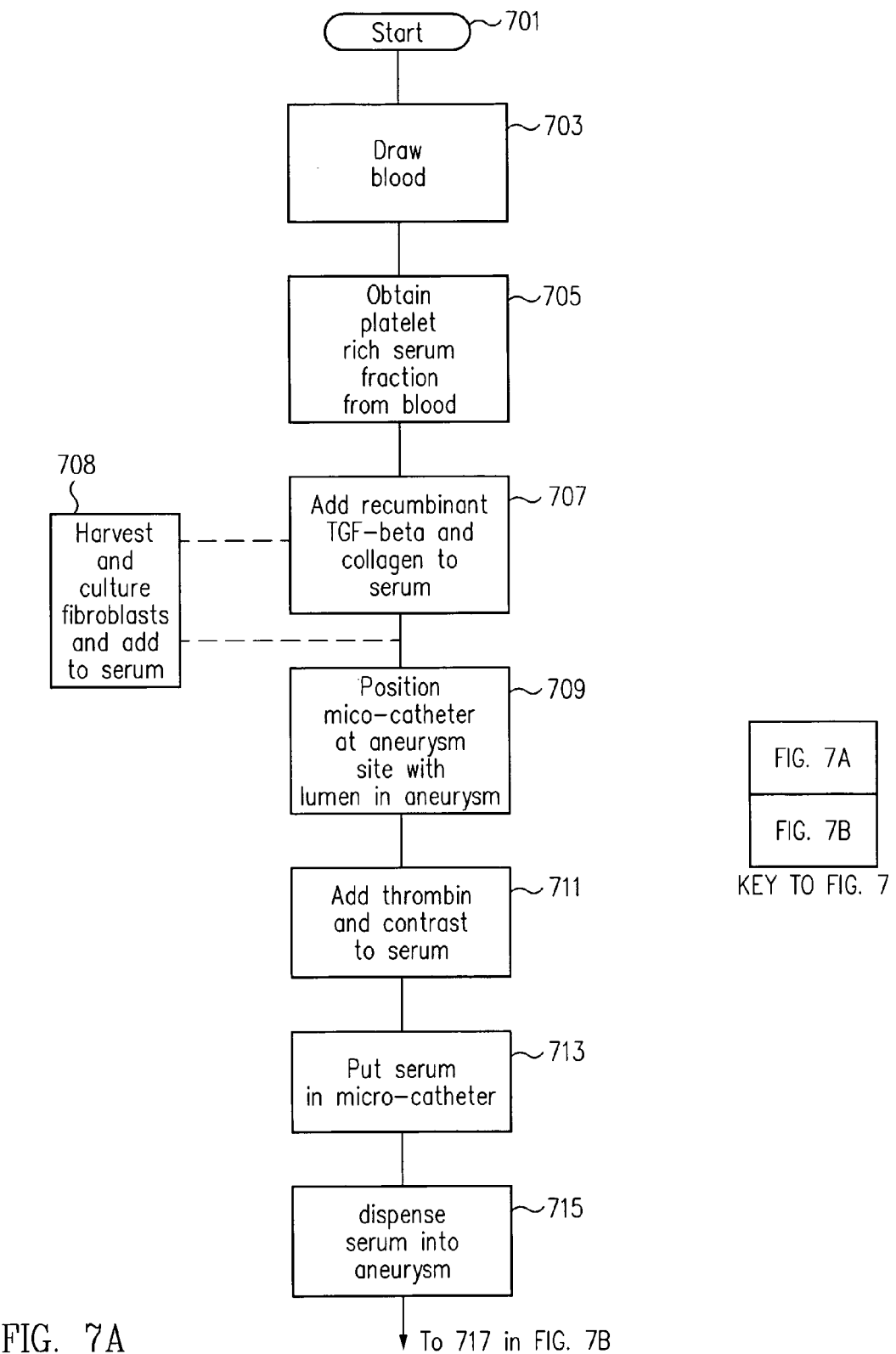
FIG. 7 shows the relationship between FIGS. 7A and 7B which together show a process flow chart of one embodiment in accordance with the present invention in which the irritant employed with the method according to the invention is a serum including the growth factor TGF-beta.
Figure 7B:
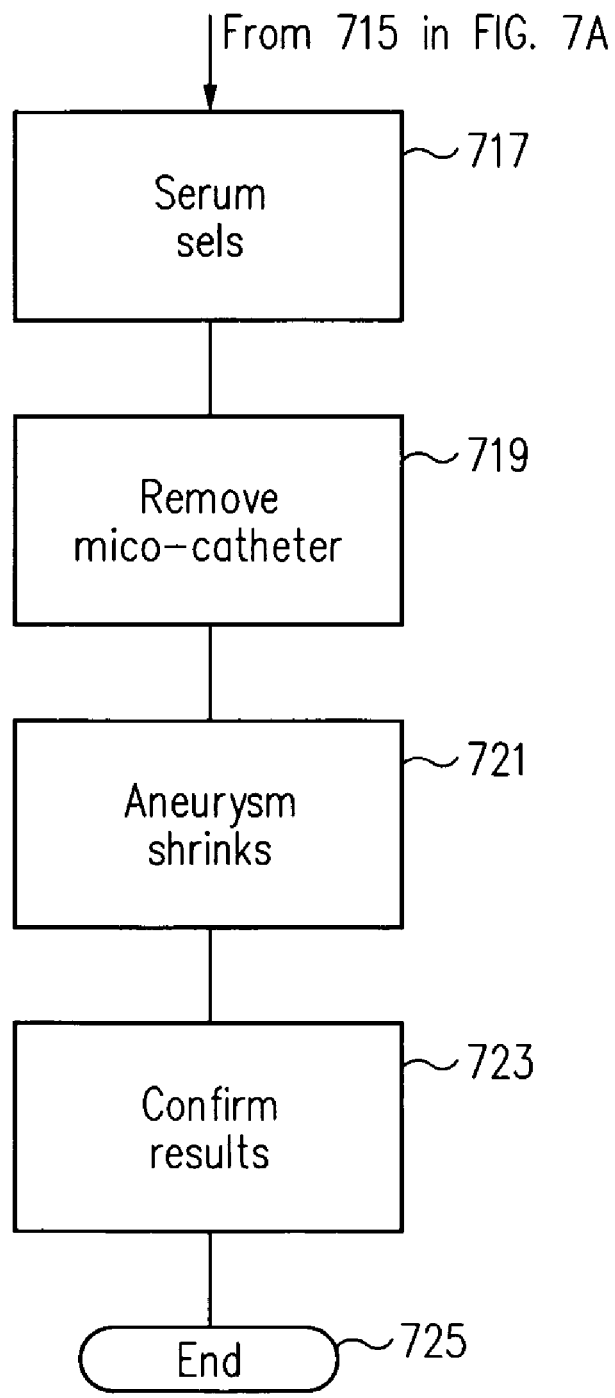

FIGS. 7A and 7B show a process flow chart of one example in which irritant 209 (FIGS. 2 to 6), in serum form, includes TGF-beta. Viewing FIGS. 7A and 7B, along with FIGS. 1 to 6, together, at start 701, the method is started. At draw blood procedure 703, blood is drawn from the patient. At obtain serum fraction procedure 705, the blood drawn at draw blood procedure 703 is centrifuged to obtain a platelet-rich serum fraction to form the basis of irritant 209 (FIGS. 2 to 6).

At add TGF-beta and collagen procedure 707, recombinant TGF-beta protein and collagen are added to the platelet-rich serum fraction of draw blood procedure 703. In one example, two nanograms to ten micrograms of TGF-beta is added per milliliter of platelet-rich serum fraction. In one example five nanograms to five micrograms of TGF-beta is added per milliliter of platelet-rich serum fraction. At this point in the process, there is an optional add fibroblasts procedure 708 at which fibroblasts can be harvested and cultured from the patient and then added to the serum of add TGF-beta and collagen 707 to intensify the eventual contractile force.

At position catheter procedure 709, micro-catheter 105 (FIG. 1) is positioned as shown in FIG. 1 in parent artery or vessel 101 such that micro-catheter tip 107 is in aneurysm 103. Returning to FIG. 7A, at add thrombin and contrast procedure 711, thrombin and contrast are added to the serum of add TGF-beta procedure 707. Thrombin is added to change the serum of add TGF-beta and collagen 707 into a gel form. The contrast, typically a radiopaque marker, is added to the serum at 10% to 50% of the usual concentration (i.e., 5% to 25%) to facilitate visualization of the irritant, and still differentiate it from the contrast injected into the parent vessel during the procedure.

At load serum procedure 713, the serum of add thrombin procedure 711 is placed in micro-catheter 105 to be used as irritant 209 (FIG. 2). Returning to FIG. 7A, at dispense serum procedure 715, the serum of add thrombin procedure 711 is dispensed as irritant 209 to form layer 211 on original aneurysm inner surface area 104 of aneurysm 103 (FIGS. 2 and 3).

Proceeding to FIG. 7B, at gel serum procedure 717, the serum of add thrombin procedure 711 gels such that layer 211 in FIG. 3 becomes a gel on inner surface 104 of aneurysm 103. At remove catheter procedure 719, micro-catheter 105 (FIG. 1) is removed from parent artery or vessel 101. Returning to FIG. 7B, at shrink procedure 721, over the course of several days to weeks, the TGF-beta causes the patients fibroblasts, whether added at add fibroblasts procedure 708 or naturally recruited to the aneurysm 103 site, to exert a contractile force on the collagen added at add TGF-beta and collagen procedure 707.

At confirm results procedure 723, the results are checked and/or confirmed. At end 725, the method ends.

Consequently, aneurysm 103 contracts or "shrinks" as shown in FIGS. 5 and 6 and discussed above, such that original aneurysm surface area 104 and original aneurysm volume 102 of aneurysm 103 decrease, thereby strengthening the artery wall, reducing the risk of rupture, and decreasing the pressure on the surrounding tissue (i.e., reducing the mass-effect).

Recall from the discussion above that a significant limitation of the prior art coil insertion method was the fact that the prior art method did not promote shrinkage of the aneurysm, or in any way address the expansion of the arterial wall at the aneurysm site. As discussed above with respect to the embodiments of the invention shown in FIGS. 1 to 6 and FIG. 7, the method according to the present invention, in contrast to the prior art, is specifically directed to shrinking the aneurysm thereby strengthening the artery wall, reducing the risk of rupture, decreasing the pressure on the surrounding tissue (i.e., reducing the mass-effect), providing at least a partial cure for the expansion of the arterial wall at the aneurysm site, and potentially reducing neurological effects due to a brain aneurysm. Consequently, in contrast to the prior art, the method according to the present invention addresses the underlying disease rather than simply treating the symptom.

In addition, using the one embodiment in accordance with the present invention discussed above, there are no coils used and therefore no risk of the coil, or ensuing thrombus, migrating from the aneurysm to the parent artery or vessel and causing a thrombo-embolic stroke, or of the coil rupturing the aneurysm. Consequently, the method according to the invention is safer than prior art methods and can be applied to more types and shapes of aneurysms than prior art methods. In addition, embodiments in accordance with the present invention can be used to treat any type of aneurysm including brain aneurysms, abdominal aneurysms and thoracic aortic aneurysms.

In addition, as discussed above, prior art coil insertion methods could only be used on relatively large aneurysms, i.e., aneurysms having diameters of three millimeters or more. In contrast to the prior art, at least one embodiment in accordance with the present invention uses a liquid or gel irritant and therefore does not rely on the use of coils, or any other rigid or semi-rigid elements with set sizes and volumes. Consequently, the method according to the present invention can be used on aneurysms of all sizes and shapes (including wide-necked and fusiform) and any aneurysm can be treated using the method according to the present invention as soon as the aneurysm is detected. Since, as discussed above, aneurysms can result in a rupture of the arterial wall, and possibly death, the fact that embodiments according to the present invention allow for early and immediate treatment provides a significant advantage over the prior art.

In another example, a polymer material is used to contract or "shrink" the aneurysm instead of an irritant. According to this example, the polymer is dispensed by a micro-catheter into an aneurysm in liquid or gel form where it adheres to the inner surface of the aneurysm. The polymer contracts or "shrinks" as it cures and hardens into its solid or semi-solid form. Since, the polymer adheres to the inner surface of the aneurysm, the aneurysm also contracts or "shrinks" with the polymer as the polymer cures. As discussed in more detail below, a remodeling balloon is used to isolate or "occlude" the aneurysm while the polymer is being dispensed, thereby preventing polymer material from entering the patient's blood stream while the polymer is still in liquid or gel form.

FIG. 8 is a side view, in cross-section, of a patient's parent artery or vessel 801 at an aneurysm 803 site including a micro-catheter 805 inserted into aneurysm 803 for dispensing a polymer, typically in liquid or gel form. Micro-catheter 805 is positioned to extend into neck 810 of aneurysm 803 such that micro-catheter tip 807 is positioned within aneurysm 803. As shown in FIG. 8, aneurysm 803 has an original, or first, aneurysm inner surface area 804 enclosing an original, or first, aneurysm volume 802.

In one example, a remodeling balloon is used seal neck 810 of aneurysm 803, and original aneurysm inner surface area 804 along with original aneurysm volume 802, during treatment. FIG. 9 is a side view, in cross-section, of parent artery or vessel 801 at aneurysm 803 including micro-catheter 805 inserted into aneurysm 803, positioned as discussed above with respect to FIG. 8, and an un-inflated remodeling balloon 901 inserted into parent artery or vessel 801 such that expansion portion 903 of remodeling balloon 901 is positioned to seal neck 810 of aneurysm 803 when remodeling balloon 901 is inflated. The operation, positioning, and use of remodeling balloons are well known to those of skill in the art and are therefore not discussed in detail.

Once remodeling balloon 901 is positioned as discussed above, remodeling balloon 901 is inflated. FIG. 10 is a side view, in cross-section, of parent artery or vessel 801 at aneurysm 803 including micro-catheter 805 inserted into aneurysm 803, positioned as discussed above with respect to FIG. 8, and remodeling balloon 901, positioned as discussed above with respect to FIG. 9, and inflated such that expansion portion 903 of remodeling balloon 901 seals neck 810 of aneurysm 803. As shown in FIG. 10 inflated remodeling balloon 901 pinches micro-catheter 805 against neck 810 of aneurysm 803 at area 1001 and pushes surface 1020 of micro-catheter 805 against parent artery or vessel 801 wall 1021 to effectively seal off and isolate aneurysm 803 and temporarily block parent artery or vessel 801. As discussed in more detail below, the isolation of aneurysm 803 and temporary blocking of parent artery or vessel 801 is performed by remodeling balloon 901 to prevent the polymer, typically applied in liquid or gel form, from draining out of aneurysm 803 and entering the blood stream before the polymer cures.

In another example, a dissolving stent (not shown) can be used for the isolation of the aneurysm (e.g., 803) and temporary blocking of the parent artery or vessel (e.g., 801) to prevent the polymer (e.g., 1109), from draining out of the aneurysm (e.g., 803) and entering the blood stream before the polymer cures. In this example, the stent material (not shown) is chosen such that the stent dissolves after a predetermined time that is greater than the curing time of the polymer (e.g., 1109).

As shown in FIG. 11, once aneurysm 803 is isolated or "occluded" by remodeling balloon 901 as discussed above, polymer 1109 is dispensed into aneurysm 803 and neck 810 of aneurysm 803 from micro-catheter tip 807 of micro-catheter 805. Polymer 1109 is chosen such that polymer 1109 readily adheres to original aneurysm inner surface area 804. In alternative embodiments, not shown, a thin layer of adhesive is applied to original aneurysm inner surface area 804 by micro-catheter 805 prior to the introduction of polymer 1109 to ensure polymer 1109 adheres to original aneurysm inner surface area 804. There are a number of reactive systems that have been developed to be good tissue sealants, i.e., adhesives. These include PMMA (polymethylmethacrylate) and cyanoacrylates.

In one example, the polymer used is a hydrophylic polymer gel with hydroxl or carboxl groups on the surface. One example of a hydrophylic polymer gel with hydroxl or carboxl groups on the surface is polyhydroxyethylmethacrylate. In other examples, the polymer can include an alginate gel or a hyaluronic acid. Other suitable polymers include silicone, urethane, epoxy, and polymethyl methacrylate (PMMA). Silicone, urethane, epoxy, and polymethyl methacrylate(PMMA) are all available in adhesive formulations, and therefore could be used as the adhesive layer discussed above as well.

In other examples, the polymer used can be one of poly tetra flourethylene (PTFE, Teflon), polyethylene, polypropylene, polysulfone. In general, any of the polymers of the epoxy, urethane, and silicone type can potentially be used. In addition, a biodegradable polymer such as the polycarprolatone (PCL) polymers can be used.

At least a thin layer 1111 of polymer 1109 substantially covers original aneurysm inner surface area 804 and neck 810 of aneurysm 803 so that there is physical contact between polymer 1109 and substantially all of original aneurysm inner surface area 804 and neck 810 of aneurysm 803.

As shown in FIG. 12, polymer 1109 is dispensed from micro-catheter tip 807 until substantially the entire original aneurysm volume 802 is filled with polymer 1109. Consequently, in this embodiment, it is virtually assured that at least a thin layer 1111 of polymer 1109 substantially covers substantially all of original aneurysm inner surface area 804 so that there is physical contact between polymer 1109 and substantially all of original aneurysm inner surface area 804.

In one example, any blood (not shown) filling original aneurysm volume 802, and trapped in aneurysm 803 prior to the filling of original aneurysm volume 802 with polymer 1109, is displaced, and forced out, from aneurysm 803 as original aneurysm volume 802 is filled with polymer 1109. This procedure is possible because most remodeling balloons are highly compliant balloons with nominal inflation pressures of 0.5 ATM. In one example, to further ensure any blood (not shown) filling original aneurysm volume 802, and trapped in aneurysm 803 prior to the filling of original aneurysm volume 802 with polymer 1109, is displaced, remodeling balloon 901 is, at first, only partially inflated such that the blood can escape, or push by, remodeling balloon 901 since remodeling balloon 901 would not tightly seal neck 810 of aneurysm 803. In one example, remodeling balloon 901 is more fully inflated once polymer 1109 has been dispensed to more tightly seal neck 810 of aneurysm 803 as polymer 1109 cures.

In other examples, aneurysm 803 is cleansed of any blood trapped (not shown) in aneurysm 803 prior to, or during, the application of polymer 1109. In one example, the cleansing of aneurysm 803 is accomplished by employing a dual lumen micro-catheter (not shown) as micro-catheter 805 such that recovery of any blood trapped in the aneurysm (not shown) can occur via one lumen (not shown), while polymer 1109 is delivered via the other. In another example, the cleansing of aneurysm 803 is accomplished before the delivery of polymer 1109 by either a single or dual lumen micro-catheter. However, even in this example, a dual lumen micro-catheter (not shown) may be desired, despite the sequential sequencing, to ensure the removed blood will "clear" the micro-catheter lumen and allow passage of polymer 1109. Dual lumen micro-catheters, their use, and their operation are well known to those of skill in art as are specific process used for cleansing trapped blood from an aneurysm. Consequently, the structure, insertion, positioning and use of a dual lumen micro-catheter and the cleansing process discussed above are not described in more detail herein to avoid detracting from the present invention.

As shown in FIG. 13, once polymer 1109 is dispensed from micro-catheter tip 807 and allowed to at least partially cure, solidify or gel, remodeling balloon 901 is deflated. Remodeling balloon 901 is then removed from parent artery or vessel 801, as shown in FIG. 14. As shown in FIG. 15, micro-catheter 805 is then also removed.

As discussed above, polymer 1109 is chosen such that polymer 1109 readily adheres to original aneurysm inner surface area 804, or an adhesive is used to ensure polymer 1109 adheres to original aneurysm inner surface area 804. In addition to its adhesive qualities, polymer 1109 is chosen from a group of polymers that contract or "shrink" as they cure. As discussed in more detail below, since polymer 1109 adheres to original aneurysm inner surface area 804, when polymer 1109 contracts, original aneurysm inner surface area 804 also contracts and thereby contracts or "shrinks" aneurysm 803. In addition, since polymer 1109 is eventually in contact with the patient's blood, any material released as polymer 1109 contracts must either be biologically inert or be released in very small quantities. As discussed above, some examples of polymers suitable for use with the present invention as polymer 1109 are hydrophylic polymer gels with hydroxl or carboxl groups on the surface. One example of a hydrophylic polymer gel with hydroxl or carboxl groups on the surface is polyhydroxyethylmethacrylate. In other examples polymer 1109 can include an alginate gel or a hyaluronic acid. Other suitable polymers include silicone, urethane, epoxy, and polymethyl methacrylate(PMMA). Silicone, urethane, epoxy, and polymethyl methacrylate (PMMA) are all available in adhesive formulations, and therefore could be used as the adhesive layer discussed above as well. In other examples, the polymer used can be one of poly tetra flourethylene (PTFE, Teflon), polyethylene, polypropylene, polysulfone. In general, any of the polymers of the epoxy, urethane, and silicone type can potentially be used. In addition, a biodegradable polymer such as the polycarprolatone (PCL) polymers can be used.

FIG. 15 is a side view, in cross-section, of parent artery or vessel 801 at aneurysm 803 site after micro-catheter 805 (FIG. 14) has been removed. As shown in FIG. 15, original aneurysm volume 802 enclosed by original aneurysm inner surface area 804 is filled with polymer 1109 and at least layer 1111 of polymer 1109 is in contact with substantially all of original aneurysm inner surface area 804.

In addition, in one example, contrast, typically a radio-paque marker (not shown), is added to polymer 1109, while polymer 1109 is in liquid or gel form, and prior to polymer 1109 being dispensed. In one example, the contrast (not shown) is added to polymer 1109 at 10% to 50% of the usual concentration to facilitate visualization of polymer 1109, and still differentiate polymer 1109 from the contrast (not shown) injected into parent artery 801 during the procedure. In addition, the physician will be able to visualize the contrast (not shown) in polymer 1109 while polymer 1109 is being dispensed, which will facilitate complete occlusion while preventing over-injection and herniation of polymer 1109 into parent artery 801. The contrast will also aid in visualizing of the treated aneurysm 803 in follow-up visits.

The process of curing polymer 1109 is now begun. Procedures for curing polymer 1109 will vary according to the specific polymer 1109 used but can include, curing by exposure to water, low temperature curing, i.e., curing at temperatures around 98.6 degrees Fahrenheit or less, higher temperature curing, or ultra-violet curing, x-ray curing and/or other radiation curing methods can be used, some of which are applied via well known specialized tools and techniques such as specialized catheter or endoscope designs. In other examples, metal flakes (not shown) or carbon (not shown) are added to polymer 1109 to absorb RF energy, microwave or MRI such that when this energy is applied to polymer 1109, heat is generated to cure polymer 1109.

FIG. 16 is a side view, in cross-section, of parent artery or vessel 801 at aneurysm 803 site with polymer 1109 in contact with substantially all of original aneurysm inner surface area 804. As discussed above, polymer 1109 is chosen such that polymer 1109 readily adheres to original aneurysm inner surface area 804, or an adhesive is used to ensure polymer 1109 adheres to original aneurysm inner surface area 804. As also discussed above, polymer 1109 is chosen from a group of polymers that contract or "shrink" as they cure. Consequently, as shown in FIG. 16, when polymer 1109 starts to cure and contract, original aneurysm inner surface area 804 also contracts down to partially contracted aneurysm inner surface area 1604 and thereby contracts or "shrinks" original aneurysm volume 802 down to partially reduced aneurysm volume 1602.

As shown in FIG. 17, as time passes, polymer 1109 fully cures and causes further contraction or "shrinkage" of partially contracted aneurysm inner surface area 1604 to contracted aneurysm inner surface area 1704 and thereby contracts or "shrinks" partially reduced aneurysm volume 1602 down to reduced aneurysm volume 1702.

In one embodiment, original, or first, aneurysm volume 802 is reduced four to twenty percent or more to contracted, or second, aneurysm volume 1702. Consequently, aneurysm 803 contracts or "shrinks" as shown in FIGS. 16 and 17 and discussed above, such that the surface area and volume of the aneurysm decreases, thereby strengthening the artery wall, reducing the risk of rupture, and decreasing the pressure on the surrounding tissue (i.e., reducing the mass-effect).

In other examples (not shown), a bioactive substance (not shown), such as the TGF-beta serum discussed above with respect to FIGS. 7A/7B or other bioactive irritant, can be added to a polymer (e.g., 1109) to increase the shrinkage of the aneurysm (e.g., 803). In one example, the bioactive substance could be formulated to be time released to the inner surface (e.g., 804/1604/1704) of the aneurysm.

The embodiment shown in FIGS. 8 to 17, like that discussed above with respect to FIGS. 1 to 6 and FIG. 7A/7B, is specifically directed to shrinking the aneurysm, thereby strengthening the artery wall, reducing the risk of rupture, decreasing the pressure on the surrounding tissue, providing at least a partial cure for the expansion of the arterial wall at the aneurysm site, and potentially reducing neurological effects due to a brain aneurysm. Consequently, in contrast to the prior art, the method according to the present invention shown in FIGS. 8 to 17 addresses the underlying disease rather than simply treating the symptom.

In addition, as with the embodiment discussed above with respect to FIGS. 1 to 6 and FIG. 7A/7B, the embodiment shown in FIGS. 8 to 17, uses no coils so there is no risk of a coil, or ensuing thrombus, migrating from the aneurysm to the parent artery or vessel and causing a thrombo-embolic stroke, or of the coil rupturing the aneurysm or of compaction of the coil within the aneurysm. Consequently, the method according to the invention shown in FIGS. 8 to 17 is safer and can be applied to more types and shapes of aneurysms than prior art methods.

In addition, like the embodiment discussed above with respect to FIGS. 1 to 6 and FIG. 7A/7B, and in contrast to the prior art, the embodiment shown in FIGS. 8 to 17 uses an initially liquid or gel polymer and therefore does not rely on the use of coils, or any other rigid or semi-rigid elements. Consequently, the method according to the present invention shown in FIGS. 8 to 17 can be used with aneurysms of all sizes and shapes (including wide-necked and fusiform) and any aneurysm can be treated using the method according to the present invention as soon as it is detected. In addition, the method according to the present invention shown in FIGS. 8 to 17 can be used to treat any type of aneurysm including brain aneurysms, abdominal aneurysms and thoracic aortic aneurysms.

This disclosure provides exemplary embodiments in accordance with the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A method for treating an aneurysm comprising:
    drawing a portion of blood from a patient;
    centrifuging said portion of blood to obtain a platelet-rich serum fraction;
    adding recombinant TGF-beta protein to said platelet-rich serum fraction;
    adding collagen to said platelet-rich serum fraction;
    adding contrast to said platelet-rich serum fraction;
    adding a gelling agent to said platelet-rich serum fraction, thereby creating an irritant serum;
    dispensing said irritant serum, as a fluid, from a micro-catheter into said aneurysm to cover at least a portion of said original aneurysm surface area with said irritant serum wherein said irritant serum covering said portion of said original aneurysm surface area is in contact with and remains in contact with said portion of said original aneurysm surface area; and said irritant serum remains in contact with said portion of said original aneurysm surface area and, said irritant serum gels on said original aneurysm inner surface area and said TGF-beta protein causes patient fibroblasts to exert a contractile force on said collagen causing a contractile force to be exerted on said original aneurysm surface area such that said original aneurysm surface area contracts to a contracted aneurysm surface area, smaller than said original aneurysm surface area, said contracted aneurysm surface area enclosing a contracted aneurysm volume that is smaller than said original aneurysm volume.

2. The method for treating an aneurysm of claim 1, wherein;
said gelling agent is thrombin.

3. A method for treating an aneurysm comprising:
drawing a portion of blood from a patient;
centrifuging said portion of blood to obtain a platelet-rich serum fraction;
adding recombinant TGF-beta protein to said platelet-rich serum fraction;
adding collagen to said platelet-rich serum fraction;
harvesting and culturing fibroblasts from said patient;
adding said harvested and cultured fibroblasts from said patient to said platelet-rich serum fraction;
adding contrast to said platelet-rich serum fraction;
adding a gelling agent to said platelet-rich serum fraction, thereby creating an irritant serum;
dispensing said irritant serum, as a fluid, from a micro-catheter into said aneurysm to cover at least a portion of said original aneurysm surface area with said irritant serum wherein said irritant serum covering said portion of said original aneurysm surface area is in contact with and remains in contact with said portion of said original aneurysm surface area; and
said irritant serum remains in contact with said portion of said original aneurysm surface area and, said irritant serum gels on said original aneurysm inner surface area and said TGF-beta protein causes said harvested and cultured fibroblasts and native patient fibroblasts to exert a contractile force on said collagen causing a contractile force to be exerted on said original aneurysm surface area such that said original aneurysm surface area contracts to a contracted aneurysm surface area, smaller than said original aneurysm surface area, said contracted aneurysm surface area enclosing a contracted aneurysm volume that is smaller than said original aneurysm volume.

4. The method for treating an aneurysm of claim 3, wherein;
said gelling agent is thrombin.

5. The method for treating an aneurysm of claim 3, wherein;
said adding recombinant TGF-beta protein to said platelet-rich serum fraction comprises adding two nanograms to ten micrograms of TGF-beta per milliliter of said platelet-rich serum fraction to said platelet-rich serum fraction.

6. The method for treating an aneurysm of claim 3, wherein;
said adding recombinant TGF-beta protein to said platelet-rich serum fraction comprises adding five nanograms to five micrograms of TGF-beta per milliliter of said platelet-rich serum fraction to said platelet-rich serum fraction.

7. A method for treating an aneurysm, said method comprising:
drawing a portion of blood from a patient;
centrifuging said portion of blood to obtain a platelet-rich serum fraction;
adding recombinant TGF-beta protein to said platelet-rich serum fraction;
adding collagen to said platelet-rich serum fraction;
adding contrast to said platelet-rich serum fraction;
adding thrombin to said platelet-rich serum fraction, thereby creating an irritant serum;
positioning a micro-catheter in a parent artery or vessel of said patient at a site of an aneurysm, said micro-catheter having a micro-catheter tip and a micro-catheter lumen, said aneurysm comprising an original aneurysm surface area enclosing an original aneurysm volume;
positioning said micro-catheter tip such that said micro-catheter lumen is situated within said original aneurysm volume;
dispensing said irritant serum from said micro-catheter, through said micro-catheter lumen, such that at least a portion of said original aneurysm surface area is covered with said irritant serum; and
removing said micro-catheter from said parent artery or vessel, wherein;
said irritant serum gels on said original aneurysm inner surface area and said TGF-beta protein causes patient fibroblasts to exert a contractile force on said collagen causing a contractile force to be exerted on said original aneurysm surface area such that said original aneurysm surface area contracts to a contracted aneurysm surface area, smaller than said original aneurysm surface area, said contracted aneurysm surface area enclosing a contracted aneurysm volume that is smaller than said original aneurysm volume.

8. The method for treating an aneurysm of claim 7, wherein;
said adding recombinant TGF-beta protein to said platelet-rich serum fraction comprises adding two nanograms to ten micrograms of TGF-beta per milliliter of said platelet-rich serum fraction to said platelet-rich serum fraction.

9. The method for treating an aneurysm of claim 7, wherein;
said adding recombinant TGF-beta protein to said platelet-rich serum fraction comprises adding five nanograms to five micrograms of TGF-beta per milliliter of said platelet-rich serum fraction to said platelet-rich serum fraction.

10. A method for treating an aneurysm, said method comprising:
drawing a portion of blood from a patient;
centrifuging said portion of blood to obtain a platelet-rich serum fraction;
adding recombinant TGF-beta protein to said platelet-rich serum fraction;
adding collagen to said platelet-rich serum fraction;
harvesting and culturing fibroblasts from said patient;
adding said harvested and cultured fibroblasts from said patient to said platelet-rich serum fraction;
adding contrast to said platelet-rich serum fraction;
adding a thrombin to said platelet-rich serum fraction, thereby creating an irritant serum;
positioning a micro-catheter in a parent artery or vessel of said patient at a site of an aneurysm, said micro-catheter having a micro-catheter tip and a micro-catheter lumen, said aneurysm comprising an original aneurysm surface area enclosing an original aneurysm volume;

positioning said micro-catheter tip such that said micro-catheter lumen is situated within said original aneurysm volume;

dispensing said irritant serum from said micro-catheter, through said micro-catheter lumen, such that at least a portion of said original aneurysm surface area is covered with said irritant serum; and removing said micro-catheter from said parent artery or vessel, wherein;

said irritant serum gels on said original aneurysm inner surface area and said TGF-beta protein causes said harvested and cultured fibroblasts and native patient fibroblasts to exert a contractile force on said collagen causing a contractile force to be exerted on said original aneurysm surface area such that said original aneurysm surface area contracts to a contracted aneurysm surface area, smaller than said original aneurysm surface area, said contracted aneurysm surface area enclosing a contracted aneurysm volume that is smaller than said original aneurysm volume.

11. The method for treating an aneurysm of claim 10, wherein;

said adding recombinant TGF-beta protein to said platelet-rich serum fraction comprises adding two nanograms to ten micrograms of TGF-beta per milliliter of said platelet-rich serum fraction to said platelet-rich serum fraction.

12. The method for treating an aneurysm of claim 10, wherein;

said adding recombinant TGF-beta protein to said platelet-rich serum fraction comprises adding five nanograms to five micrograms of TGF-beta per milliliter of said platelet-rich serum fraction to said platelet-rich serum fraction.

* * * * *